United States Patent [19]

Wright et al.

[11] 4,350,492

[45] Sep. 21, 1982

[54] METHOD FOR PREPARING TISSUE HEART VALVE

[75] Inventors: John T. M. Wright, Huntington; George M. Acosta, Long Beach, both of Calif.

[73] Assignee: Vascor, Inc., Anaheim, Calif.

[21] Appl. No.: 295,427

[22] Filed: Aug. 24, 1981

[51] Int. Cl.³ .................. D01C 3/00; A61F 1/22
[52] U.S. Cl. .......................... 8/94.11; 3/1.4; 3/1.5
[58] Field of Search .................. 8/94.11; 3/1.4, 1.5

[56] References Cited

U.S. PATENT DOCUMENTS

| 3,570,014 | 3/1971 | Hancock | 3/1.5 |
| 3,755,823 | 9/1973 | Hancock | 8/94.11 |
| 3,966,401 | 6/1976 | Hancock et al. | 8/94.11 |
| 4,050,893 | 9/1977 | Hancock et al. | 8/94.11 |

OTHER PUBLICATIONS

R. Gorlin and S. G. Gorlin, "Hydraulic Formula For Calculation of the Area of the Stenotic Mitral Valve, Other Cardiac Valves, And Central Circulatory Shunts. I.", Am. Heart Journal, 41, 1 (1951).

Michael V. Cohen and Richard Gorlin, "Modified Orifice Equation for the Calculation of Mitral Valve Area," Am. Heart Journal, 84, 839 (1972).

Primary Examiner—Maria Parrish Tungol
Attorney, Agent, or Firm—W. R. Eberhardt

[57] ABSTRACT

A method for preparing an aortic heart valve for implantation wherein the area of the septal shelf of the right coronary cusp extending into the valve orifice is substantially reduced. The excised value is prepared for fixation by pressurizing the valve to close the valve cusps, and thereafter inverting the aortic vestibule tissue over a valve stent or other cylindrical form circumscribing the valve. As the vestibule tissue is inverted, the septal shelf muscle is pulled toward the outside wall of the valve. When the septal shelf has been displaced to the maximum extent possible while maintaining coaption of the valve leaflets, the valve is fixed with a tanning solution. The resulting valve, after being trimmed and mounted for implantation, has improved flow characteristics.

29 Claims, 7 Drawing Figures

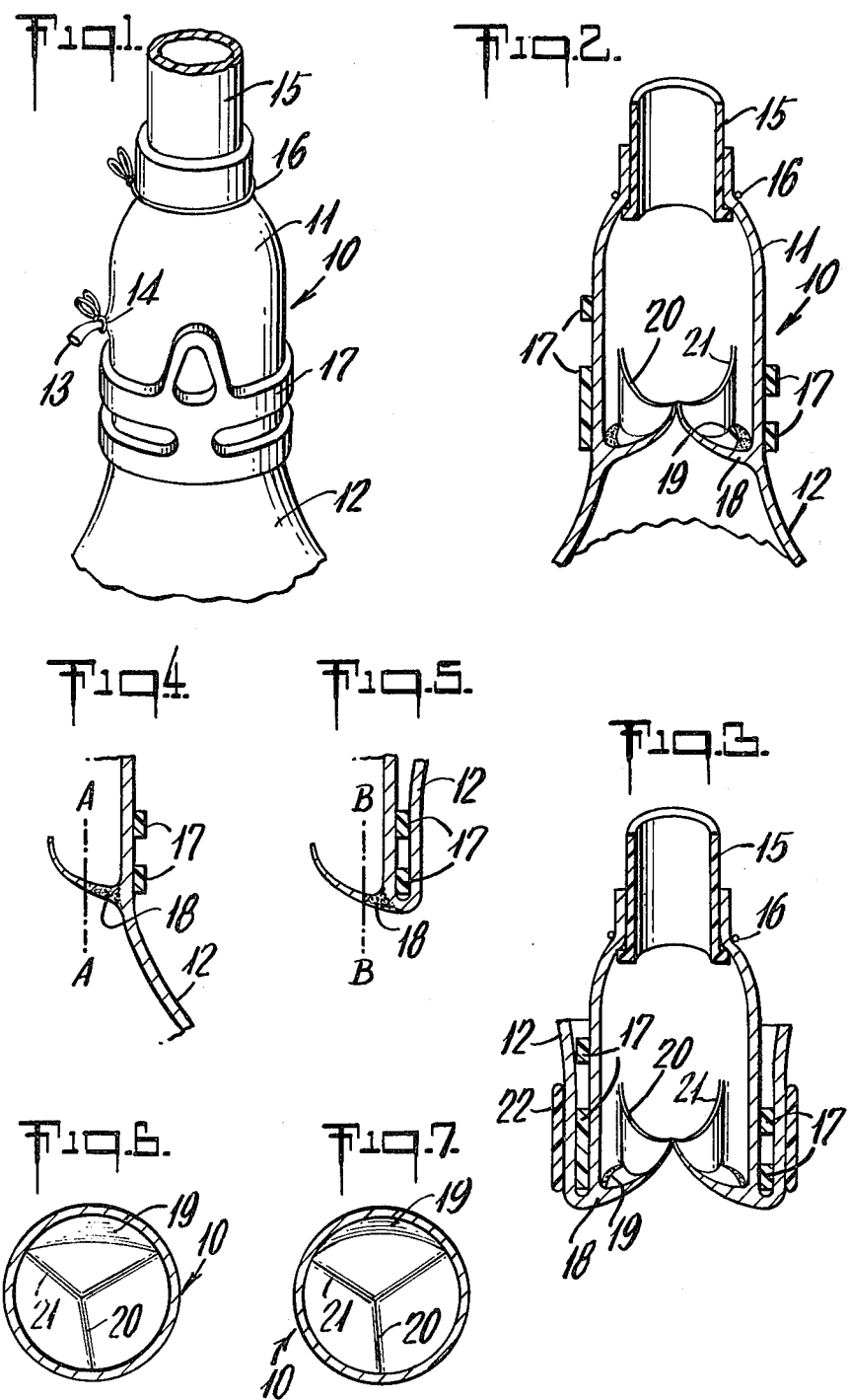

METHOD FOR PREPARING TISSUE HEART VALVE

BACKGROUND OF THE INVENTION

1. Field of the Invention

This invention relates to the preparation of natural tissue for implantation, and more particularly, to the preparation for implantation of aortic heart valves having improved flow characteristics.

2. Description of Prior Art

Natural valves taken from animals, particularly porcine aortic valves, have been used for a number of years for replacement of diseased valves in humans. The valves are excised from the animal heart, fixed in an appropriate tanning fluid such as glutaraldehyde or formaldehyde, and mounted on a framework or stent for subsequent implantation. During the fixation procedure, it is necessary that coaption of the valve cusps be maintained in order to assure proper valve function after implantation. Originally, coaption was achieved by packing the valve with cotton, and more recently, by pressurizing the valve with the tanning solution. Pressure fixation is the preferred method and is described in detail in U.S. Pat. No. 4,050,893, incorporated herein by reference.

The right coronary cusp of a porcine aortic valve is identified by the presence of a muscle referred to as the septal shelf. The septal shelf forms part of the right coronary cusp leaflet and protrudes into the valve orifice, reducing the effective maximum orifice size of the valve. Fixation of the valve by either the cotton packing or pressure technique fixes the septal shelf in its natural position.

Valves having improved flow characteristics have been produced by surgically removing the right coronary valve cusp and septal shelf attached thereto, and replacing it with a similarly sized non-coronary cusp from another valve. The cusp replacement is done following fixation of the valve, and the resulting modified valve has a larger effective orifice and improved flow characteristics due to the absence of the septal shelf. Although this procedure is effective to produce an improved aortic valve, it significantly increases valve manufacturing costs in terms of labor, materials, lost productivity, and rejected goods.

It is accordingly an object of the present invention to provide a method for preparing an aortic valve for implantation which eliminates or substantially reduces the effect of the septal shelf. It is a further object of this invention to provide an aortic valve having improved flow characteristics relative to conventionally fixed valves. It is a further object of this invention to eliminate or reduce the effect of the septal shelf on valve performance without resorting to surgical modification of the valve. These and other objects of the invention will be apparent from the ensuing description and claims.

SUMMARY OF THE INVENTION

Aortic heart valves fixed in accordance with the present invention are characterized by having a septal shelf which, instead of protruding into the valve orifice, is positioned entirely or to a major extent as part of the valve wall. Such valves are obtained by a method of fixation wherein the excised valve is pressurized to inflate the ascending aorta and close the valve cusps, whereupon a cylindrical form is placed snugly around the valve with the base of the cylinder adjacent the base of the valve cusps. The aortic vestibule tissue extending below the cusps is thereupon extended outward beyond the base of the form, pulling the septal shelf of the right coronary cusp toward the wall of the valve. Maximum displacement of the septal shelf is obtained while maintaining coaption of the valve leaflets. The valve is fixed in its extended condition and with the valve cusps coapted. After fixation, the valve is trimmed and mounted on a stent in accordance with conventional procedures for subsequent implantation.

DESCRIPTION OF DRAWINGS

FIG. 1 is a view in perspective of an excised aortic valve secured to a fluid inlet tube and with a cylindrical form in place prior to fixation.

FIG. 2 is a longitudinal sectional view of the assembly of FIG. 1 taken through the midline of the right coronary cusp.

FIG. 3 is a longitudinal sectional view of the assembly of FIG. 1 after the aortic vestibule tissue has been extended to the outside of the cylindrical form.

FIG. 4 is a fragmentary view of FIG. 2 showing the right coronary valve cusp in cross section.

FIG. 5 is a fragmentary view of FIG. 3 showing the right coronary valve cusp in cross section.

FIG. 6 is a bottom plan view of a representative aortic porcine heart valve fixed in accordance with the prior art.

FIG. 7 is a bottom plan view of a representative aortic porcine heart valve fixed in accordance with the present invention.

DESCRIPTION OF INVENTION

With reference to FIG. 1, an aortic valve 10 is excised from the donor heart along with a segment of the ascending aorta 11 and a portion of the aortic vestibule 12. In preparation for fixation, the aortic vestibule and valve annulus are preferably disected to remove a substantial portion of fresh myocardial tissue and reduce the thickness of these areas to approximately 1 mm. The coronary arteries as illustrated at 13 are tied off at 14 and the valve secured to fluid inlet tube 15 by tying the ascending aorta at 16 as illustrated.

The valve is pressurized with moist air, saline, or other inert fluid through the fluid inlet tube to close the valve cusps and distend the body of the valve to its normal diameter. The applied pressure is preferably within the range of from about 20 to 150 mm Hg and most preferably within the physiological range of from about 80 to 120 mm Hg. While higher pressures are not recommended, lower pressures which are sufficient to coapt the valve cusps may be used.

The pressurized valve is fitted with a circumferential cylindrical form illustrated in FIG. 1 as valve stent 17. The cylindrical form is selected to fit snugly over the inflated valve in the area of the valve cusps. Since the cylindrical form is used only to provide support for the valve during fixation as hereinafter described, and does not become part of the finished valve, the cylindrical form may be a regular cylinder or any other convenient configuration. A valve stent provides a convenient cylindrical form for use in the present invention as illustrated in the Figures, but this is not to imply that a valve stent must be used for this purpose.

The base of the cylindrical form, i.e., the end distal from the ascending aorta, is positioned adjacent the base of the valve cusps as illustrated in FIG. 2. In FIG. 2, the valve is sectioned through the right coronary cusp to illustrate the thickened area forming the septal shelf as indicated in cross section at 18 and in perspective as surface 19. The coapted edges of two of the three valve cusp leaflets are illustrated at 20 and 21 in FIG. 2.

After the cylindrical form has been correctly sized and positioned, and while the valve continues to be pressurized with moist air or other inert fluid, the aortic vestibule tissue is inverted over the base of cylindrical form 17 as illustrated in FIG. 3. The vestibule tissue is pulled taut around the base of the cylindrical form, especially in the area of the septal shelf, while taking care not to disrupt coaption of the valve cusps. The inverted tissue is secured around the base of the cylindrical form by means of encircling band 22 or functionally equivalent means. Surprisingly, a substantial portion of the septal shelf area can be drawn to the wall of the valve from its normal position extending into the valve orifice. This effect is most clearly illustrated in FIGS. 4 and 5.

FIG. 4 is a fragmentary view of valve wall and septal shelf in cross section in its normal position corresponding to FIG. 2. The edge of the septal shelf extending into the valve orifice is indicated by dashed line A—A. FIG. 5 is a similar view in cross section after the aortic vestibule has been inverted over the cylindrical form. The edge of the septal shelf extending in the valve orifice is indicated by dashed line B—B. The extent to which the septal shelf has been withdrawn from the valve orifice area is readily apparent in a comparison of these Figures.

Upon positioning the valve as illustrated in FIG. 3 and determining that coaption of the valve cusps remains intact, the fluid pressure is released and the valve is fixed with a tanning solution in accordance with conventional procedures. In a preferred method, the fixative solution is 0.2% aqueous glutaraldehyde buffered to a pH of about 7.4. The valve is submerged in the fixative solution and pressurized with fixative solution introduced through fluid inlet tube 15 at room temperature and for about 24 hours. If shorter times are desired, the temperature of the fixative solution may be increased above room temperature, for example 35° to 45° C. During the fixation process, the valve may be initially pressurized to physiological pressures of about 80 to 120 mm Hg and maintained under this pressure during the entire period of fixation. Alternatively, the pressure may be pulsed in accordance with the method of U.S. Pat. No. 3,966,401, or other variations in the applied pressure may be utilized. For example, the valve may initially be pressurized to from 0.5 to 5 mm Hg which is sufficient to close the valve cusps, and maintained at this pressure for a period of 0.2 to 5 hours. Thereafter, the pressure is preferably increased to at or near physiological values to fully expand the valve and the fixation process is continued for the balance of the required period. The thin tissue of the valve cusp leaflets is fixed more quickly than the thicker walls of the valve, and when the pressure is increased after the initial low pressure period, the walls of the valve are sufficiently pliable to expand to the normally full diameter experienced under physiological pressures. The initial fixation at low pressures may be desirable to reduce stress in the more delicate cusp leaflet tissue until the tissue has been at least partially fixed.

Other variations in the fixation process, including the use of other fixative compositions, temperature, pressure, and the like may be utilized at the discretion of the practitioner as will be readily appreciated by those skilled in the art.

Referring now to FIG. 6, there is illustrated a plan bottom view of the inlet side of a valve fixed in accordance with prior art technique. Essentially, the prior art method involved correctly fixation of a valve suspended from a fluid inlet tube and under sufficient pressure to close the valve cusps as disclosed, for example, in U.S. Pat. No. 4,050,893. The area of septal shelf 19 extending into the valve orifice, and the resulting reduction in effective orifice area, is readily apparent. FIG. 7 is a similar view of a valve fixed in accordance with the method of the present invention wherein septal shelf 19 has been drawn to the edge of the valve with a resulting increase in effective valve orifice area.

The valves prepared in accordance with the method of the present invention are visually and functionally equivalent to those obtained by prior art methods except for the reduction in septal shelf area and the improvement in effective valve orifice and valve flow characteristics. In practice, the extent to which the septal shelf may be withdrawn from the valve orifice area will vary according to the individual characteristics of the valve, particularly the area and thickness of the natural septal shelf. In many cases, valves prepared in accordance with the present invention will have no significant amount of septal shelf remaining in the orifice area. In all cases, the amount of septal shelf extending into the orifice area is substantially less than would have existed had the valve been fixed according to prior art methods.

EXAMPLE

A series of porcine aortic heart valves sized 29 to 35 mm were fixed in accordance with the present invention, and the flow characteristics compared to comparably-sized valves fixed in accordance with prior art techniques. Valves fixed according to the present invention were inflated through the ascending aorta with moist air at 80 mm Hg, and the aortic vestibule tissue inverted over an appropriately-sized stent positioned around the outside of the valve. The valve cusp tissue and the septal shelf of the right coronary cusp were drawn to the outside of the valve to the maximum extent possible while maintaining coaption of the cusp leaflets, and secured in this position by a polypropylene band positioned to encircle the aortic vestibule tissue.

The valve thus secured was immersed at room temperature in 0.2% aqueous glutaraldehyde fixative solution buffered to a pH of 7.4, and pressurized to 80 mm Hg with additional glutaraldehyde solution through the aorta of the valve. The fixation was continued for 24 hours whereupon the valve was removed, mounted on a conventional cloth covered stent, and stored for future testing.

Valves fixed according to the prior art were prepared by pressure fixation in a like manner except the aortic vestibule tissue and the valve cusps remained in their natural configuration.

Flow characteristics of the valve as indicated by the effective orifice area were determined in a pulsatile flow test wherein physiological saline is pumped through the valve by means of a piston pump having a stroke displacement of 60 ml and operating at a rate of 150 strokes per minute. The simulated cardiac output is thus 9 liters per minute, while the mean flow rate during the positive stroke corresponding to the systolic phase of the cardiac cycle is 300 ml per second. The mean pressure gradient across the valve during the positive stroke cycle is measured in mm Hg, and the effective orifice area of the valve calculated according to the following equation derived by Gorlin and Gorlin, Am. Heart J. 41, 1 (1951), using the empirical constant 37.9 derived by Cohen and Gorlin, Am. Heart J., 84 839 (1972):

$$\text{Orifice Area} = \frac{CO}{37.9(\sqrt{\Delta P})}$$

wherein CO equals cardiac output during the diastolic phase, or 300 ml/sec in the test method, and $\Delta P$ equals the measured pressure gradient.

The results obtained with the series of valves prepared according to the present invention and according to the prior art as described above are presented in Table I.

TABLE I

| | Effective Valve Orifice Area, cm$^2$ | | | | |
| --- | --- | --- | --- | --- | --- |
| | Prior art | | This Invention | | |
| Valve Size | No. tested | Avg. area | No. tested | Avg. area | % Improvement |
| 29 | 9 | 1.99 | 3 | 2.26 | 14 |
| 31 | 5 | 2.35 | 3 | 2.59 | 10 |
| 33 | 5 | 2.62 | 3 | 3.14 | 20 |
| 35 | 3 | 2.81 | 4 | 3.38 | 20 |

The increase in effective valve orifice area evidenced by the valves of the present invention over prior art valves represents significantly improved flow characteristics in terms of valve capacity and pressure gradient.

Processing valves in accordance with the method of the present invention and while using a valve stent as the cylindrical form significantly reduces the complexity and time of subsequently mounting the valve on a stent by configuring the fixed valve to the standard geometrical size and shape of the stent. There is accordingly a preference for using a stent of the appropriate size as the cylindrical form when preparing the valve for fixation according to the present invention. In addition, the scalloped configuration of the stent allows the coronary artery remnants to be located between the stent commissure posts, and the open design of the stent is desirable to provide the fixative solution with ready access to the outside surface of the valve.

We claim:

1. A method of fixing a natural tissue heart valve for implantation comprising
   excising the valve from the donor heart together with adjacent ascending aorta and vestibule tissue;
   pressurizing the valve through the ascending aorta to coapt the valve cusp leaflets;
   placing a cylindrical form around the valve with the base of the form aligned with the base of the valve cusps;
   extending the vestibule tissue outward beyond the base of the cylindrical form, simultaneously pulling the septal shelf toward the outside edge of the valve while maintaining coaption of the valve cusp leaflets;
   fixing the valve in its extended state and while the leaflets are coapted by treatment with a tanning solution.

2. The method of claim 1 wherein the valve is pressurized with moist air.

3. The method of claim 1 wherein the valve is pressurized to from about 20 to 150 mm of Hg.

4. The method of claim 1 wherein the valve is pressurized to the physiological range of from about 80 to 120 mm of Hg.

5. The method of claim 1 wherein the cylindrical form is configured as a heart valve stent.

6. The method of claim 1 wherein the vestibule tissue is inverted over the base of the cylindrical form.

7. The method of claim 1 wherein the valve is fixed with a tanning solution under hydrostatic pressure to maintain coaption of the valve cusp leaflets.

8. The method of claim 7 wherein the hydrostatic pressure is from about 0.5 to 150 mm Hg.

9. The method of claim 7 wherein the hydrostatic pressure is within the physiological range of from about 80 to 120 mm Hg.

10. The method of claim 7 wherein the hydrostatic pressure is initially within the range of from about 0.5 to 5 mm Hg for about 0.2 to 5 hours, and is thereafter increased to from about 80 to 120 mm Hg.

11. The method of claim 1 wherein the tanning solution is aqueous glutaraldehyde.

12. A method for improving the flow characteristics of a natural tissue heart valve intended for implantation which comprises drawing the septal shelf of the right coronary cusp toward the valve wall to the maximum extent possible while maintaining coaption of the valve cusps, and thereupon fixing the valve with a tanning solution.

13. The method of claim 12 wherein the valve is an aortic porcine heart valve.

14. The method of claim 12 wherein the valve is pressurized to coapt the valve cusp leaflets while the septal shelf is drawn toward the valve wall.

15. The method of claim 14 wherein the valve is pressurized with moist air at from about 20 to 150 mm Hg.

16. The method of claim 12 wherein the valve is pressurized with the tanning solution during fixation to maintain coaption of the valve cusp leaflets.

17. A method of preparing an aortic porcine heart valve for implantation in a human comprising the steps of
   excising from a donor heart the aortic valve including a portion of the ascending aorta on one side and the vestibule tissue on the other side;
   pressurizing the valve through the ascending aorta to close the valve cusps and inflate the valve to its substantially normal diameter;
   placing a cylindrical form snugly around said inflated valve, the base of said form being aligned with the base of the valve cusps;
   inverting the vestibule tissue over the base of said form, simultaneously pulling the septal shelf of the right coronary cusp toward the wall of the valve while maintaining coaption of the valve leaflets;
   securing the vestibule tissue in its inverted state over the cylindrical form;
   fixing the valve in a tanning solution while maintaining coaption of the valve cusp leaflets; and,
   thereafter trimming and mounting the valve on a stent for subsequent implantation.

18. The method of claim 17 wherein said valve is pressurized with moist air at from about 20 to 150 mm Hg.

19. The method of claim 17 wherein the valve is pressurized to the physiological range of from about 80 to 120 mm Hg.

20. The method of claim 17 wherein the cylindrical form is configured as a valve stent.

21. The method of claim 17 wherein the vestibule tissue is secured in its inverted state by means of an encircling band.

22. The method of claim 17 wherein the valve is fixed with a tanning solution under hydrostatic pressure to maintain coaption of the valve cusp leaflets.

23. The method of claim 22 wherein the hydrostatic pressure is from about 0.5 to 150 mm Hg.

24. The method of claim 23 wherein the hydrostatic pressure is within the physiological range of from about 80 to 120 mm Hg.

25. The method of claim 23 wherein the hydrostatic pressure is initially within the range of from about 0.5 to 5 mm Hg for about 0.2 to 5 hours, and is thereafter increased to from about 80 to 120 mm Hg.

26. The method of claim 17 wherein the tanning solution is aqueous glutaraldehyde.

27. A natural tissue heart valve prepared for implantation by the process of claim 1.

28. A natural tissue heart valve having improved flow characteristics prepared by the process of claim 12.

29. An aortic porcine heart valve prepared for implantation by the process of claim 17.

* * * * *